United States Patent [19]

Hamajima et al.

[11] Patent Number: 5,236,427
[45] Date of Patent: Aug. 17, 1993

[54] ABSORBENT ARTICLE

[75] Inventors: Mitsugu Hamajima, Kamimikawa; Masahito Tanaka, Ichikai; Fumie Yanagida, Kamimikawa; Minoru Nakanishi, Ichikai, all of Japan

[73] Assignee: KAO Corporation, Tokyo, Japan

[21] Appl. No.: 739,230

[22] Filed: Aug. 1, 1991

[30] Foreign Application Priority Data

Aug. 1, 1990 [JP] Japan .................. 2-204163

[51] Int. Cl.⁵ .................. A61F 13/15; A61F 13/20
[52] U.S. Cl. .................. 604/378; 604/358; 604/368; 604/382
[58] Field of Search ............ 604/367, 378, 358, 369, 604/373–374, 382, 368

[56] References Cited

U.S. PATENT DOCUMENTS

| | | | |
|---|---|---|---|
| 4,673,402 | 6/1987 | Weisman et al. | 604/378 |
| 4,846,813 | 7/1989 | Raley | 604/378 |
| 5,147,345 | 9/1992 | Young et al. | 604/358 |

FOREIGN PATENT DOCUMENTS

| | | |
|---|---|---|
| 56-6099 | 2/1981 | Japan . |
| 56-97448 | 8/1981 | Japan . |
| 61-22854 | 1/1986 | Japan . |

Primary Examiner—Randall L. Green
Assistant Examiner—A. Zuttarelli
Attorney, Agent, or Firm—Birch, Stewart Kolasch & Birch

[57] ABSTRACT

An absorbent article comprising a liquid permeable outer material, a liquid retentive absorbent article and a liquid-impermeable antileakage material, and formed in a substantially vertically elongated shape, wherein the absorbent element comprises a diffusing absorbent sheet and an absorbent retentive sheet positioned at the rear of the diffusing absorbent sheet and:

(a) the diffusing absorbent sheet is a sheet having a hydrophilicity ($\cos \theta$) of 0.5 to 1 and a Klemm absorption velocity in the longitudinal direction of at least 40 mm/minute, and (b) the absorbent retentive sheet is a sheet comprising an aggregate of fibers having a capillary osmotic pressure of 4000 to 15000 dyne/cm² and containing 10 to 100% by weight, based on the fiber aggregate, of a highly water-absorbent polymer having a physiological saline absorption of 40 to 70 g/g and a physiological saline absorption velocity of at least 2 ml/0.3 grams polymer·minute.

18 Claims, 5 Drawing Sheets

ABSORBENT ARTICLE

BACKGROUND OF THE INVENTION

1. Field of the Invention

The present invention relates to absorbent articles typified by sanitary napkins, paper diapers and pads for incontinent people. More particularly, the present invention relates to absorbent articles having a high absorbency and improved properties of absorbing body fluids, particularly absorption velocity, diffusing capacity, inhibition of reflow of the fluid from the absorbent element and inhibition of leakage.

2. Description of the Prior Art

Various absorbent articles have been proposed for the purpose of improving the absorption of body fluids and various improvements have been developed. Most of the improvements relate to an improvement in the absorption velocity, inhibition of reflow of the fluid from the absorbent element to the surface, prevention of leakage and reduction of stickiness to the body.

For example, as for the material of the absorbent, it was proposed to absorb and retain the fluid in a highly absorbent polymer by a physicochemical effect, i.e. by ionic osmotic pressure, thereby improving the absorption capacity and also preventing the reflow of the fluid instead of using hydrophilic absorbent paper or pulp which absorbs and retains the fluid in physical fine spaces. In fact, the absorbency was improved by this proposal and at present, an absorbent element comprising a combination of pulp and a highly water-absorbent polymer is used for most of the absorbent articles. However, the prevention of leakage, even by such absorbent articles, is still insufficient, as suggested by the fact that the main reason for dissatisfaction of the absorbent articles resides in the leakage. Namely, the body fluid absorption velocity of the highly water-absorbent polymer which absorbs and retains fluid by ionic osmotic pressure is limited and, in addition, no body fluid can be absorbed unless the polymer is wetted with the body fluid. Therefore, the highly water-absorbent polymer must have been used in combination with pulp or the like having a high water absorption velocity. However, the pulp used in combination with the polymer is extremely reduced in its strength when it is wetted and the strength is not recovered, though it exhibits some compression and bending recoveries when it is dry. When stress is applied to the wet pulp, compression deformation (hereinafter referred to as the twist) thereof is caused to seriously reduce the absorption space. In addition, the body fluid once absorbed is easily pressed out by the twist and reabsorption velocity after the twist is seriously reduced. Thus in such a case, the absorbent element is twisted before the highly absorbent polymer sufficiently exhibits its absorbency and the twist frequently causes the leakage.

Techniquies of making up such defects of the absorbent elements are proposed in, for example, Japanese Utility Model Publication No. 6099/1981, Japanese Patent Laid-Open No. and 22854/1986 and Japanese Patent Laid-Open No. 97748/1981.

Figure 5:
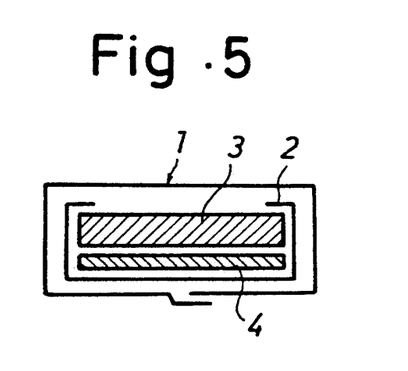
FIGS. 5, 6 and 7 are cross sections corresponding to that of FIG. 1 which show conventional sanitary napkins.

(1) A sanitary napkin disclosed in Japanese Utility Model Publication No. 6099/1981 is composed of a liquid-permeable surface material 1, an absorbent element 2 mainly comprising hydrophilic fibers and a liquid-impermeable back sheet 3 as shown in FIG. 5, and an elastic porous element 4 (such as a foam) having shape-retaining properties is provided in the absorbent element 2 or at the rear of it in order to prevent the absorbent element 2 from being deformed.

Figure 6:
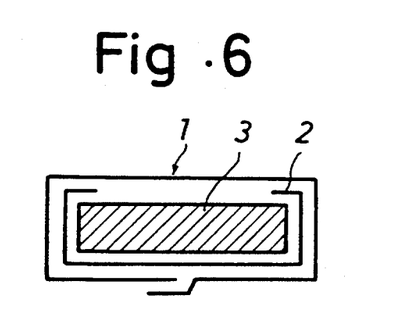

(2) A sanitary napkin disclosed in Japanese Patent Laid-Open No. 22854/1986 is the same as the sanitary napkin (1) except that the hydrophilic fibers used as the absorbent element 2 are replaced by an elastic porous element (such as urethane skeleton foam or polyester fiber aggregate bonded with a binder).

Figure 7:
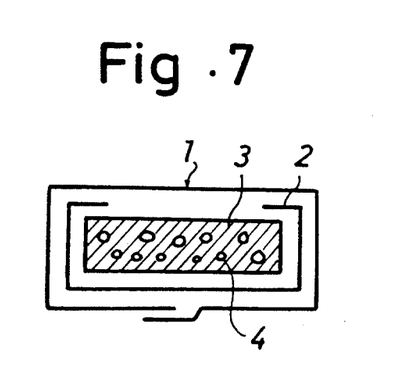

(3) A sanitary napkin disclosed in Japanese Patent Laid-Open No. 97748/1981 comprises hydrophilic fibers and/or water-absorbent polymer uniformly dispersed in the cells of an elastic porous element 4 used as an absorbent element 2 as shown in FIG. 7.

Although the shape of the sanitary napkin (1) is retained as a whole, the elastic porous element 4 arranged in parallel with the absorbent element 2 has insufficient hydrophilic properties and its skeletal structure is not effective in absorbing or retaining the body fluid and, therefore, it has substantially no absorbent or retentive properties per se. In addition the absorbent element 2 per se mainly comprising the hydrophilic fibers has no recovery properties. Therefore, when stress is applied to the sanitary napkin, the twist and permanent set in fatigue of the absorbent element 2 are caused to make the exhibition of a sufficient absorbing effect of the absorbent element 2 impossible.

In the sanitary napkin (2), although the elastic porous element used as the absorbent element 2 has excellent recovery from deformation, the liquid retentivity thereof is poor as in the napkin (1) and such an absorbent article is practically useless for this purpose.

Although the sanitary napkin (3) has liquid absorbency and liquid retentivity superior to those of the napkin (2) to some extent, its performance is yet insufficient for use as the absorbent article, since the liquid retentivity of the elastic porous element which is the main component of the absorbent element 2 is quite poor.

Under these circumstances, the absorbent articles comprising a combination of the above-described pulp and highly absorbent polymer are now mainly used.

Various ideas were proposed for inhibiting the backing of the liquid with a surface sheet even after the reflow of the liquid from the absorbent element in the currently mainly used absorbent articles. The surface sheet is made of a nonwoven fabric comprising a hydrophobic material (such as polypropylene staple, polyethylene staple or polyester staple), instead of an ordinary hydrophilic material (such as rayon staple). In such a case, a space of hydrophobic atmosphere is formed between the surface of the user's body and the absorbent element to reduce the stickiness of the surface. In particular, absorbent articles in which the surface sheet is made of a hydrophobic sheet (film) having open cells were recently proposed. Since the hydrophobic material having open cells is used as the surface sheet, the liquid is not retained in the surface sheet and it is effective in preventing sticking. However, the liquid permeability is a requirement contradictory to the prevention of the reflow of the liquid and these two requirements cannot be completely satisfied at the same time. Namely, as the space of the hydrophobic atmosphere is increased, the open cell part is decreased to ensure the prevention of the reflow of the liquid but the permeation of the liquid is inhibited. Thus by merely adjusting the size of the space, the permeability to the liquid and the prevention of the reflow of the liquid cannot be easily and effectively attained at the same time.

SUMMARY OF THE INVENTION

An object of the present invention is to provide an absorbent article capable of rapidly absorbing an excreted body fluid to diffuse it into the whole absorbent article, taking advantage of the absorbent function of the absorbent element, particularly, a highly absorbent polymer, thereby inhibiting the reflow of the fluid into the surface layer and leakage thereof.

After intensive investigations made for the purpose of developing an absorbent article which has an absorbent capacity higher than that of ordinary absorbent articles, an extremely reduced reflow of the fluid to the surface, a reduced stickiness of the surface thereof and a remarkably reduced leakage and which can be thus comfortably used, the inventors have found that the purpose can be attained by employing an absorbent element, a part of which is made of a specified diffusing absorbent sheet and a specified absorbent retentive sheet.

The present invention has been completed on the basis of the above-described finding and provides an absorbent article comprising a liquid-permeable outer material, a liquid-impermeable antileakage material and a liquid-retentive absorbent element interposed between said materials, and formed in a substantially vertically elongated shape, characterized in that the absorbent element mainly comprises a diffusing absorbent sheet and an absorbent retentive sheet positioned at the rear of the diffusing absorbent sheet and:

(a) the diffusing absorbent sheet is a sheet having a hydrophilicity (cos $\theta$) of 0.5 to 1 and a Klemm absorption velocity in the longitudinal direction of at least 40 [mm/min], and (b) the absorbent retentive sheet is a sheet comprising an aggregate of fibers having a capillary osmotic pressure of 4000 to 15000 [dyn/cm$^2$] and containing 10 to 100% by weight, based on the fiber aggregate, of a highly water-absorbent polymer having a physiological saline (isotonic sodium chloride solution) absorption of 40 to 70 [g/g] and a physiological saline absorption velocity of at least 2 [ml/0.3 g polymer·min].

In the absorbent article of the present invention, the body fluid which has passed through the surface material is rapidly diffused in the whole absorbent element by the diffusing absorbent sheet of the element and, at the same time, penetrates into the inside, and the penetrated body fluid rapidly passes through a fiber aggregate sheet, i.e. absorbent retentive sheet, to enclose the body fluid captured by the highly absorbent polymer.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 1 is a cross section of a part of a transverse section of a sanitary napkin which is an example of the absorbent articles of the present invention.

FIG. 2 is a cross section corresponding to that of FIG. 1 which shows another example of the absorbent articles of the present invention.

FIG. 3 is an enlarged cross section of an absorbent retentive sheet of the sanitary napkin shown in FIG. 1.

FIG. 4 is an enlarged perspective view of a surface sheet of the sanitary napkin shown in FIG. 1.

DETAILED DESCRIPTION OF THE INVENTION

The present invention will now be described with reference to FIGS. 1 to 16.

The absorbent article of the present invention comprises a liquid-permeable outer material (surface sheet) 1, a liquid-retentive absorbent element 2 and a liquid-impermeable antileakage material (antileakage sheet) 3 and is formed in a substantially vertically elongated shape as shown in FIG. 1. The absorbent article is worn in such a manner that the surface sheet 1 is brought into contact with the skin of the user and the antileakage sheet 3 is brought into contact with the underwear. The absorbent element 2 is interposed between the surface sheet 1 and the antileakage sheet 3. As shown in FIG. 1, the rear surface, the entire sides and the periphery of the surface of the absorbent element 2 are covered with the antileakage sheet 3 and the entire surfaces of them are covered with the surface sheet 1. The central part of the surface of the absorbent element 2 is directly covered with the surface sheet 1 so that the body fluid will be directly passed into the absorbent element 2. The rear of the surface sheet 1 has three longitudinal belt-like adhesive parts 4 which are covered with a release paper 5. Numeral 6 refers to a joint.

The absorbent element 2 of the present invention mainly comprises a diffusing absorbent sheet 21 and an absorbent retentive sheet 22 positioned at the rear of the diffusing absorbent sheet 21.

The diffusing absorbent sheet 21 comprises a laminate of three layers of a wet-process nonwoven fabric made of hydrophilic fibers.

The diffusing absorbent sheet has a hydrophilicity (cos $\theta$) of 0.5 to 1 and a Klemm absorption velocity in the longitudinal direction of at least 40 mm/min), still preferably a hydrophilicity (cos $\theta$) of 0.6 to 1 and a Klemm absorption velocity in the longitudinal direction of at least 50 [mm/min]. The hydrophilicity (cos $\theta$) is an indication of the compatibility of the liquid with the sheet. The Klemm absorption velocity is an indication of the diffusibility of the liquid in the sheet. When the hydrophilicity (cos $\theta$) is less than 0.5 or the Klemm absorption velocity is less than 40 [mm/min], the diffusibility of the liquid or absorption velocity will be lowered to make an effective exhibition of the absorption function of the highly absorbent polymer, which will be described below, impossible.

The material of the diffusing absorbent sheet 21 in the present invention is not particularly limited as long as the sheet satisfies the requirements of the above-described properties. Examples of preferred materials include foams of synthetic polymers such as polyurethane, polystyrene, polyethylene, polyester, polyvinyl alcohol, butadienestyrene rubber (SBR) and nitrile-butadiene rubber; fiber aggregates produced by bonding synthetic fibers (such as polyethylene (PE), polypropylene (PP) or polyethylene terephthalate (PET)) by heat fusion or with an adhesive; and fiber aggregates produced by bonding hydrophilic fibers (such as rayon fibers or pulp fibers) by thermocompression or with an adhesive.

When the diffusing absorbent sheet 21 of the present invention is one made of a hydrophobic material, it is preferred to impart hydrophilic properties to it with a surfactant to improve the hydrophilicity (cos $\theta$) and Klemm absorption velocity. The surfactant usable for this purpose may be any hydrophilic surfactant having both a lipophilic group and a hydrophilic group. Preferred are anionic surfactants and nonionic surfactants having a high molar number of ethylene oxide added thereto. Examples of preferred surfactants include sulfosuccinic esters, alkyl ether sulfates, polyoxyethylene alkyl ethers, polyoxyethylene alkylphenol ethers and glycerol fatty acid esters. They may be used either singly or in the form of a mixture of surfactants suitably selected from among them. Those capable of imparting the above-described hydrophilicity (cos $\theta$) to the sheet in an amount of 0.05 to 1% by weight are still preferred.

The diffusing absorbent sheet 21 made of a hydrophilic material is preferred, since the treatment thereof with a wetting agent is unnecessary and the hydrophilic properties are stable during use for a long period of time and reabsorption. Examples of preferred hydrophilic materials include wet-process nonwoven fabrics produced by bonding hydrophilic fibers (such as pulp fibers, rayon fibers or Vinylon) by fusion or with an adhesive or the like. Still preferred are wet-process blended pulp paper made from pulp and rayon fibers. To obtain the antileakage and absorbent properties, it is preferred to use a wet-process blended pulp paper comprising a mixture of rayon fibers of thinner than 3 deniers and pulp and containing 30 to 90% of the rayon fibers or, in other words, having a mixing weight ratio of the rayon to the pulp of 30/70 to 90/10. The rayon fibers have a roundness of the cross section thereof of preferably 0.5 or less, still preferably 0.4 or less.

The diffusing absorbent sheet 21 may be either a laminate of two or more layers or a single layer as shown in FIG. 1 or 2. It preferably comprises a laminate of two or more diffusing absorbent sheets having different Klemm absorption velocities. In the diffusing absorbent sheet 21 comprising the two or more layers, the absorption velocity gradient is regulated in such a manner that the absorption velocity is increased from the surface side (upper layer) toward the rear side (lower layer) so that the body fluid will be spread toward the lower layer which is not close to the body.

The higher the liquid permeability of the diffusing absorbent sheet toward the absorbent retentive sheet, the better. For this purpose, the liquid permeation time (as determined by a method which will be described below) is preferably within 200 sec, still preferably within 150 sec.

The diffusing absorbent sheet 21 must rapidly spread the body fluid in the whole absorbent element. To more effectively prevent leakage on both sides, the diffusing velocity of the diffusing absorbent sheet 21 in the longitudinal direction is preferably different from that in the transverse direction. The ratio of the length to the width of the spread liquid area determined one minute after dropping a physiological saline on the diffusing absorbent sheet 21 (longitudinal/transverse ratio) is preferably at least 1.2, still preferably 1.3 to 3. The longitudinal direction of the diffusing absorbent sheet 21 preferably coincides with that of the absorbent article.

The diffusing absorbent sheet 21 preferably has deformation recovery. More specifically, the sheet 21 has a residual strain after compression in a wet state, i.e. after the absorption of the liquid, of not higher than 0.3.

The absorbent retentive sheet 22 in the present invention is a laminate comprising sheets 22 A each comprising an aggregate of fibers having a capillary osmotic pressure of 4,000 to 15,000 dyn/cm$^2$ and a highly absorbent polymer 22 B having a physiological saline absorption of 40 to 70 [g/g] and a velocity of absorbing the physiological saline of at least 2 [ml/0.3 g polymer·min] interposed in an amount of 10 to 100% by weight between the sheets 22 A (refer to FIG. 3).

The sheets 22 A containing the highly absorbent polymer 22 B interposed therebetween them have a capillary osmotic pressure of 4,000 to 15,000 dyn/cm$^2$, preferably 4,000 to 12,000 dyn/cm$^2$. When the capillary osmotic pressure is below 4,000 to 12,000 dyn/cm$^2$, the absorbent retentive sheet 22 has difficulty absorbing the liquid from the diffusing absorbent sheet 21 and, on the contrary, when it exceeds 15,000 dyn/cm$^2$, the movement of the liquid into the highly absorbent polymer 22 B becomes undesirably not smooth.

The highly absorbent polymer 22 B has a physiological saline absorption of preferably 40 to 70 [g/g]. When the absorption exceeds 70 [g/g], the surface of the absorbent polymer is not dry when the absorbent article is wet and the liquid cannot be effectively diffused. On the contrary, when the absorption is less than 40 [g/g], the absorption per se undesirably insufficient. The highly absorbent polymer 22 B has a velocity of absorbing a physiological saline of at least 2 [ml/0.3 g polymer·min], preferably at least 3 [ml/0.3 g polymer·min]. When the absorption velosity is below 2 ml/0.3 g polymer min), the liquid cannot be effectively moved, the absorption of the absorbent polymer is insufficient and water undesirably pools in the absorbent element.

10 to 100% by weight, preferably 30 to 80% by weight, of the highly water-absorbent polymer 22 B is interposed between the sheets 22 A, each comprising a fiber aggregate. When the amount of the polymer 22 B exceeds 100% by weight, a gel blocking occurs after the absorption and, on the other hand, when it is below 10% by weight, the amount of the retained liquid is undesirably insufficient. The highly water-absorbent polymer may be uniformly arranged between the sheets or its concentration may be partially nonuniform. From the viewpoint of the flow behavior of the liquid in the absorbent article, a structure in which the amount of the highly water-absorbent polymer is increased at both ends of the sheet is still preferred.

The capillary osmotic pressure and the quantity and velocity of absorbing a physiological saline are determined based on the values measured with apparatus shown in FIGS. 9 and 10 by methods which will be described below.

Capillary Osmotic Pressure (dyn/cm²)

Figure 9:
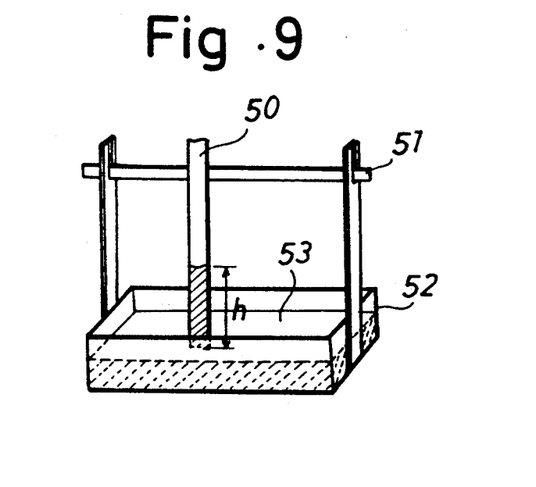
FIG. 9 is a perspective view of an apparatus used for the determination of the capillary osmotic pressure.

An apparatus shown in FIG. 9 was used for determining the capillary osmotic pressure.

A fiber aggregate sheet to be used as the absorbent retentive sheet was cut into ten absorbent retentive sheets 50 having a size of 250 mm×20 mm. Then the piece 50 was hung and both ends thereof were fixed in such a manner that a support 51 would not be loosened. A physiological saline 53 was placed to a depth of 40 mm in a rectangular vessel 52 having a size of 300×100×50 (depth) mm and the test piece 50 was immersed in the physiological saline 53. 60 min after the immersion, the maximum liquid absorption height was measured. This procedure was repeated by using the ten test pieces 50 and the average of the observed values was calculated and substituted for the average maximum liquid absorption height h₆₀ mm in the following formula to determine the capillary osmotic pressure P (dyn/cm²):

capillary osmotic pressure $P = \rho g h_{60}$ wherein:
P represents the capillarly osmotic pressure (dyn/cm²),
$\rho$ represents a specific gravity (g/cm³) of a physiological saline,
g represents $9.8 \times 10^2$ cm/S², and
$h_{60}$ represents the absorption height (cm) of a physiological saline after 60 min.

Quantity of Absorption [g/g]

1 g of the highly water-absorbent polymer 22 B was dispersed in a large excess of a physiological saline to sufficiently swell the former with the latter. Then the polymer 22 B was filtered through an 80-mesh wire gauze and weighed. The absorption was given in terms of the weight thus obtained.

Absorption Velocity

Figure 10:
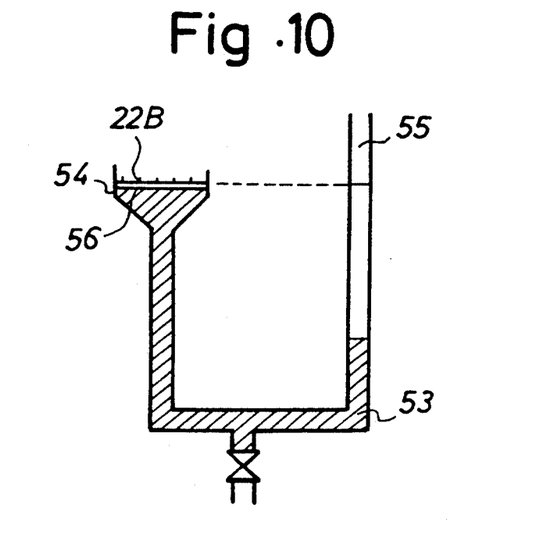
FIG. 10 is a cross section of an apparatus used for the determination of the absorption velocity.

The absorption velocity was determined with an apparatus shown in FIG. 10.

The level of a physiological saline 53 in a buret 55 was set flush with a sample mount 54. 0.3 g of the highly absorbent polymer 22 B was uniformly sprayed over a glass filter 56 having a diameter of 70 mm in the mount 54. The absorption velocity [ml/0.3 g polymer·min] was given in terms of the volume of the physiological saline 53 absorbed by the polymer 22 B in 1 min.

The material of the absorbent retentive sheet 22 is not particularly limited as long as it satisfies the above-described conditions. Examples of preferred fiber aggregate usable as the material of the sheet include those produced by bonding synthetic fibers (such as polyethylene (PE), polypropylene (PP) or polyethylene terephthalate (PET)) by heat fusion or with an adhesive and those produced by bonding hydrophilic fibers (such as rayon fibers or pulp fibers) by heat compression or with an adhesive.

The highly water-absorbent polymer 22 B used in the present invention is preferably a polymer such as a cross-linked high-molecular polyacrylic acid salt capable of absorbing and retaining a large amount of a liquid by ionic osmotic pressure and preventing the liquid from causing leakage even under pressure. It must have a function of rapidly absorbing the liquid from the sheet having fine open spaces. In addition, it is preferred that the surface of the polymer sheet be kept dry even after the swelling and that it do not disturb the movement of the liquid.

Since such absorption functions cannot be easily exhibited when the highly water-absorbent polymer has a uniform crosslinked structure, it is preferred to give rise to a crosslinking density gradient. Preferred highly water-absorbent polymers having a crosslinking density gradient are those having a polyacrylic acid salt skeleton and a neutralization condition ranging from pH 6 to pH 7.5. The crosslinking density gradient of the highly water-absorbent polymer can be realized by dispersing or suspending an aqueous solution of an acrylic acid salt containing a water-soluble radical initiator in a nonaqueous solvent in the presence of a protective colloid to cause polymerization, then adjusting the water content of the resulting polyacrylic acid salt to 10 to 40% by weight and further reacting the polyacrylic acid salt with a crosslinking agent capable of reacting with a functional group of the polyacrylic acid salt to further crosslink the surface thereof.

Such crosslinking agents are preferably water-soluble compounds having at least two functional groups reactive with the carboxyl group. Examples of them include polyglycidyl ethers such as ethylene glycol diglycidyl ether, polyethylene glycol diglycidyl ether and glycerol triglycidyl ether; epoxides of halohydrins such as epichlorohydrin and α-methylchlorohydrin; polyaldehydes such as glutaraldehyde and glyoxal; polyols and polyamines. Among them, polyglylcidyl ethers such as ethylene glycol diglydicyl ether are preferred.

The absorption velocity varies depending on the particle diameter. As the particle diameter of the highly water-absorbent polymer is reduced, the absorption velocity is increased but gel blocking is liable to occur during the absorption. To avoid the gel blocking, the average particle diameter of the highly absorbent polymer is preferably 20 to 200 μm, still preferably 50 to 150 μm. The term "gel blocking" indicates reduction in diffusibility of the liquid when it is retained. To satisfy both the absorption capacity of the liquid and the diffusibility of the liquid when it is retained, the structure of the absorbent retentive sheet 22 is preferably such that the highly water-absorbent polymer 22 B is interposed between the sheets 22 A comprising a fiber aggregate (see FIG. 3). At least two sheets comprising a fiber aggregate are necessary and they may be put together to form a laminate. They are preferably fixed by embossing and spiral hot melting so that the polymer will not fall away from the sheet.

The laminate comprising the sheets 22 A and the highly water-absorbent polymer 22 B interposed between them may be used either singly or in combinations of several laminates. For a sanitary napkin, only one laminate is enough.

The absorbent article of the present invention has a remarkably improved capacity of absorbing a body fluid because of a synergistic effect obtained by combining the above-specified diffusing absorbent sheets 21 with the absorbent retentive sheet 22. Namely, in a sanitary napkin which is one embodiment of the absorbent article of the present invention, the diffusing absorbent sheets 21 quite effectively diffuse the fluid over the whole absorbent retentive sheet 22 and this sheet 22 comprising the highly absorbent polymer 22 B is capable of exhibiting the maximum absorbent and retentive capacity. Thus the fluid which was excreted and then passed through the diffusing absorbent sheet 21 can be rapidly gelled. In other words, the excreted body fluid can be rapidly absorbed and diffused and the absorbed body fluid can be rapidly enclosed.

In the absorbent article of the present invention, it is also important to combine the absorbent element 2 with the surface sheet (top sheet) 1 in order to obtain a sufficient effect of the absorbent element 2.

When the absorbent article 2 contains a large quantity of the fluid absorbed therein, the surface sheet capable of inhibiting the reflow of the fluid from the absorbent article 2 toward the surface and rapidly introducing the fluid into the absorbent article 2 is preferred in order to facilitate the exhibition of the absorbent retentive effect of the absorbent element 2 and to increase the antileakage capacity. As for the surface sheet 1, a sheet shown in FIG. 4 which comprises a nonwoven fabric having a high liquid permeability and a hydrophobic film inhibiting the retention of the fluid is preferred. The surface sheet shown in FIG. 4 is a laminate of two layers, i.e. a film layer 11 to be brought into contact with the skin of the user and a hydrophilic fiber aggregate layer 12 to be brought into contact with the absorbent element 2. The surface sheet 1 has numerous concavities 1 A (having a diameter of 0.5 to 5 mm) each of which narrows towards the center thereof and each of which has openings 1 C in the film layer 11 on the inclined walls 1 B thereof. The openings 1 C are closed by the fiber aggregate layer 12. Since the four faces of the inclined wall 1 B forming the concavity 1 A are inclined so that the concavity 1 A narrows towards the center, the openings 1 C are not covered even when the surface sheet 1 is compressed.

By using the surface sheet 1, the fluid excreted from the body can be rapidly introduced into the absorbent element 2 and the reflow of the fluid can be inhibited even after a large amount of the fluid has been absorbed therein. Thus the absorbent article of the present invention having a high absorbent retentive capacity can be made far thinner than conventional absorbent articles while, maintaining its antileakage effect and accordingly, it easily fits the body to make the user comfortable.

EXAMPLES

The following Examples will further illustrate the absorbent article of the present invention. Although the description will be made with reference to sanitary napkins, the present invention is also applicable to paper diapers or the like.

I. The diffusing absorbent sheets, absorbent retentive sheets and surface sheets used in the Examples and Comparative Examples were prepared and their functions were determined as follows:

(1) PREPARATION OF DIFFUSING ABSORBENT SHEETS

1 Diffusing absorbent sheet (A)

75 parts of rayon fibers for wet process (trade name: SA Rayon mfd. by Daiwabo Rayon) having a thickness of 1.7 denier, a length of 7 mm and a roundness of the section of the fiber (determined as will be described below) of 0.21, 25 parts of pulp fibers and 10 parts of polyvinyl alcohol (hereinafter referred to as PVA) (trade name: Gosenol P-250 mfd. by Nippon Synthetic Chemical Industry Co., Ltd.) used as a binder were dispersed in water. A paper was prepared from them and dried to obtain a pulp/rayon blended paper (diffusing absorbent sheet (A)) having a basis weight of 25 g. The roundness of the rayon fiber was determined as follows:

Determination of roundness

An electron photomicrograph of the section of the fiber was taken and the image thereof was analyzed with an image analyzer (Avio EXCEL of Nippon Avionics Co., Ltd.). The roundness was calculated from the analytical results by the equation given below. The roundness of each of 100 samples was determined and the average of them was employed as the roundness.

$$\text{Roundness} = 4 \times \pi \times A/L^2$$

wherein:
A represents the cross-sectional area of the fiber, and
L represents the circumferential length of the section of the fiber.

2 Diffusing absorbent sheet (B)

50 parts of SA rayon for wet process having a thickness of 1.7 denier, a length of 7 mm and a roundness of the section of the fiber of 0.21, 50 parts of pulp fibers and 10 parts of PVA (Gosenol P-250) as a binder were dispersed in water. A paper was prepared from them and dried to obtain a pulp/rayon blended paper (diffusing absorbent sheet (B)) having a basis weight of 25 g.

3 Diffusing absorbent sheet (C)

70 parts of SA rayon for wet process (trade name: Corona (SB) Rayon mfd. by Daiwabo Rayon) having a thickness of 1.7 denier, a length of 7 mm and a roundness of the section of the fiber of 0.68, 30 parts of pulp fibers and 10 parts of PVA (Gosenol P-250) as a binder were dispersed in water. A paper was prepared from them and dried to obtain a pulp/rayon blended paper (diffusing absorbent sheet (C)) having a basis weight of 25 g.

4 Diffusing absorbent sheet (D)

A wet-process rayon spun bond nonwoven fabric having a thickness of 2 denier and a basis weight of 30 g (trade name: TCF 703 mfd. by Futamura Chemical Industries Co., Ltd.) was used as the diffusing absorbent sheet (D).

5 Diffusing absorbent sheet (E)

A wet-process rayon spun bond nonwoven fabric having a thickness of 2 denier and a basis weight of 50 g (trade name: TCF 405 mfd. by Futamura Chemical Industries Co., Ltd.) was used as the diffusing absorbent sheet (E).

6 Diffusing absorbent sheet (F)

An absorbent paper having a basis weight of 25 g obtained from pulp by the wet papermaking process was used as the diffusing absorbent sheet (F).

7 Diffusing absorbent sheet (G)

10 parts of SA rayon for wet process having a thickness of 1.7 denier, a length of 7 mm and a roundness of the section of the fiber of 0.21, 90 parts of pulp fibers and 10 parts of PVA (Gosenol P-250) as the binder were dispersed in water. A paper was prepared from them and dried to obtain a pulp/rayon blended paper (diffusing absorbent sheet (g)) having a basis weight of 25 g.

8 Diffusing absorbent sheet (H)

50 parts of a wet-process rayon (trade name: Corona (SB) Rayon mfd. by Daiwabo Rayon) having a thickness of 3 denier, a length of 7 mm and a roundness of the section of the fiber of 0.68, 50 parts of pulp fibers and 10 parts of PVA (Gosenol P-250) as a binder were dispersed in water. A paper was prepared from them and dried to obtain a pulp/rayon blended paper (diffusing absorbent sheet (H)) having a basis weight of 25 g.

9 Diffusing absorbent sheet (I)

A sheet prepared from a ground pulp and having a basis weight of 300 g/m$^2$, a thickness of 5 mm and a density of 0.06 g/cm$^3$ was used as a diffusing absorbent sheet (I).

(2) The hydrophilicity (cos $\theta$), Klemm absorption velocity, liquid permeation time, spreading ratio of the longitudinal length to the transverse length of the spread area of the liquid (longitudinal/transverse ratio) and residual strain after compression of each of the diffusing absorbent sheets A through I prepared as described above were determined by the following methods to obtain the results given in Table 1.

1 Determination of hydrophilicity (cos $\theta$) and Klemm absorption velocity

Figure 11:
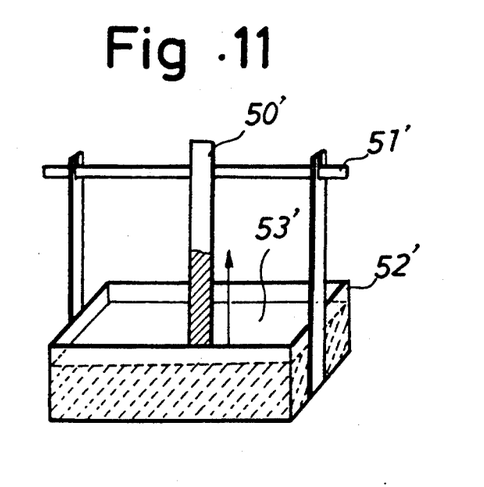
FIG. 11 is a perspective view of an apparatus used for the determination of the hydrophilicity and Klemm absorption velocity.

The hydrophilicity (cos $\theta$) and Klemm absorption velocity were determined with an apparatus shown in FIG. 11.

The diffusing absorbent sheet was cut into test pieces 50' having a size of 250 mm×20 mm. The test piece 50' was hung from a support 51' and the upper and lower ends thereof were fixed so that it would not be loosened as shown in FIG. 11. A physiological saline 53' as a test liquid was placed to a depth of 40 mm in a rectangular vessel 52' having a size of 300×100×50 (depth) mm and the test piece 50' was immersed in the physiological saline 53'. The height of the absorbed liquid level of the test piece 50' from the physiological saline level was determined 1 min and 60 min after the immersion of the test piece 50'. This test was repeated by using 10 test samples in total and the physiological saline 53' absorption height after 1 min (h$_1$) and that after 60 min (h$_{60}$) were given in terms of the averages of them. The Klemm absorption velocity h$_1$ (mm/min) was given in terms of h$_1$ (absorption height after 1 min).

Then a similar procedure to that described above was repeated except that the physiological saline 53' was replaced by ethanol (EtOH) (special grade chemical mfd. by Wako Pure Chemical Industries, Ltd.) to determine the height of EtOH absorbed in the test piece 50' after 60 min. The absorption height of EtOH after 60 min (h$_{60}'$) was given in terms of the average height of 10 test pieces 50'.

The hydrophilicity (cos $\theta$) ($\theta$ being a contact angle between the physiological saline and the test piece) of the test piece 50' with the physiological saline 53' was calculated by the equation given below.

This method of calculating the hydrophilicity (cos $\theta$) was developed according to the so-called powder method:

$$\cos \theta = \frac{h_{60} \times \gamma_1 \times \rho_2}{h'_{60} \times \gamma_2 \times \rho_1}$$

wherein:

h$'_{60}$ represents EtOH absorption height after 60 min (cm), $\gamma_1$ represents the surface tension of EtOH (dyn/cm), p1 $\rho_1$ represents the specific gravity of EtOH (g/cm$^3$), h$_{60}$ represents physiological saline absorption height after 60 min (cm), $\gamma_2$ represents the surface tension of the physiological saline (dyn/cm), and p1 $\rho_2$ represents the specific gravity of the physiological saline (g/cm$^3$).

2 Determination of liquid permeation time

Figure 12:
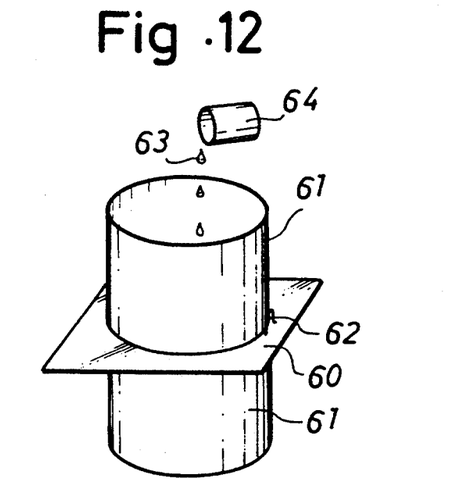
FIG. 12 is a perspective view of an apparatus used for the determination of the liquid permeation time.

The liquid permeation time was determined with an apparatus shown in FIG. 12.

The diffusing absorbent sheet was cut into test pieces 60 having a size of 50 mm×50 mm. Then the test piece 60 was fixed between upper and lower glass pipes 61 and 61 having an inner diameter of 35 mm as shown in FIG. 12. It was fixed on both sides with clips through a silicone rubber 62 so that the liquid would not leak laterally. 10 g of an 85% aqueous glycerol solution 63 having a composition given below as the test solution was gently poured in a 20-ml beaker 64. After the completion of addition of the 85% aqueous glycerol solution, a time taken for at least 50%, on the basis of the opening area of the glass pipe 61, of the surface of the test piece to appear was determined. The time thus determined was the liquid permeation time.

Preparation of the test solution (85% aqueous glycerol solution)

85 g of glycerol (mfd. by Wako Pure Chemical Industries, Ltd.) was mixed with 15 g of ion-exchanged water. 0.3 g of Blue No. 1 for food (mfd. by Tokyo Kasei Kogyo K.K.) was added to the mixture to color it blue.

3 Spreading ratio (longitudinal/transverse) of the spread liquid area

Figure 13:
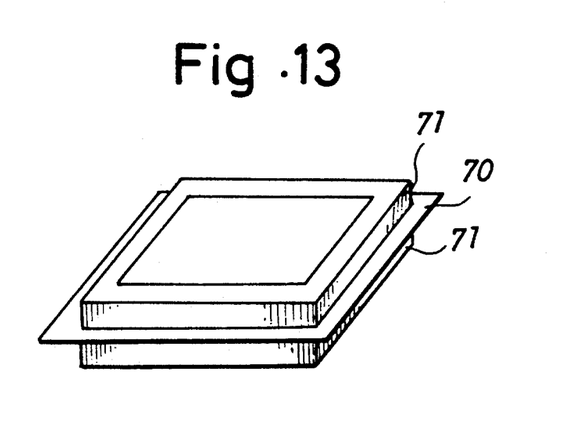
FIG. 13 is a perspective view of an apparatus used for the determination of the spread ratio (longitudinal/transverse) of the spread liquid area.

The spreading ratio of the spread liquid area was determined with an apparatus shown in FIG. 13.

In the test, the diffusing absorbent sheet was cut into test pieces 70 having a size of 120 mm×120 mm. The test piece 70 was fixed between two acrylic frames 71 and 71 having a size of 110 mm×110 mm×10 mm (thickness) having an opening of a size of 100 mm×100 mm so that the piece 70 would not be loosened. Then a drop (0.04 g) of a physiological saline was gently added from a pipet placed 10 mm above the test piece 70. One min after the addition, the maximum length and width of the area of the liquid spread on the test piece 70 were measured. This procedure was repeated by using 10 test pieces and the average values of these pieces were employed and the longitudinal/transverse spreading ratio of the spread liquid area was calculated by the equation given below. In the diffusing absorbing sheet, the longitudinal direction of the test piece 70 was made to coincide with that of the sanitary napkin.

Spreading ratio of spread liquid area (longitudinal/transverse)=[maximum spreading width in the longitudinal direction (mm)]/[maximum spreading width in the transverse direction (mm)]

4 Residual strain after compression in wet state

The diffusing absorbent sheet was cut into test pieces having a size of 50 mm×50 mm. The thickness $l_0$ ($\mu$m) of the test piece in a dry state under a load of 5 g/cm$^2$ was determined. Then the test piece was wetted by immersing it in a physiological saline for 1 min. The wet test piece 80 was compressed under the maximum load of 300 g/cm$^2$ under conditions comprising a compression rate of 5 mm/min, a compression area of 10 cm$^2$ and a disk having a radius of 17.8 mm with a Tensilon compression tester. After the compression, the test piece was recovered at the rate equal to that described above. In this step, the thickness ($l_1$) ($\mu$m) of the test piece in a wet state under a load of 5 g/cm$^2$ was determined. The residual strain after compression of the test piece in a wet state was calculated by the following equation:

Residual strain after compression of the test piece in a wet state $= l_0 - l_1/l_0$ wherein:

$l_0$ represents the thickness ($\mu$m) under a load of 5 g/cm$^2$ in a dry state and $l_1$ represents the thickness ($\mu$m) under a load of 5 g/cm$^2$ in a wet state after compression.

(3) Preparation of absorbent retentive sheets

1 Absorbent retentive sheet (A)

Hot melt Topko P 618 B (mfd. by Toyo Petrolite Co., Ltd.) was spirally sprinkled at a rate of 10 g/cm$^2$ over an absorbent paper having a capillary osmotic pressure of 5,000 dyn/cm$^2$ and a basis weight of 33 g/cm$^2$ and then 40 g/cm$^2$ of a highly water-absorbent polymer A prepared by a process described below was sprinkled over it. Thereafter the same absorbent paper as that described above was placed on the highly water-absorbent polymer (A) to obtain an absorbent retentive sheet (A) comprising the absorbent papers and the highly water-absorbent polymer A interposed between them. Process for producing highly water-absorbent polymer A:

Sodium acrylate having a monomer concentration of 45% by weight and a degree of neutralization, $\alpha$, of 0.7 was polymerized to obtain a polymer. The water content of the polymer was adjusted to 30% by weight. Then ethylene glycol diglycidyl ether was added to the polymer so that its concentration in the polymer would be 1,000 ppm, thereby obtaining a polymer having a crosslinked structure, a cross-linking gradient and an average particle diameter of 80 $\mu$m. As for the absorption capacity of the polymer, it had a physiological saline absorption of 50 [g/g] and an absorption velocity of 6.2 [ml/0.3 g polymer.min].

2 Absorbent retentive sheet (B)

An absorbent retentive sheet (B) was produced in the same manner as that of the absorbent retentive sheet (A) except that a high water-absorbent polymer (B) prepared by a process described below was used. Process for producing highly water-absorbent polymer (B):

This polymer was produced in the same manner as that of the absorbent retentive sheet (A) except that ethylene glycol was added not after the completion of the polymerization but to the aqueous monomer solution prior to the polymerization and that the crosslinking was conducted in the course of the polymerization of the monomer to obtain a uniform crosslinked structure. The average particle diameter of the polymer was 80 $\mu$m. The polymer will be referred to as the "highly water-absorbent polymer (B)". As for the absorption capacity of the polymer, it had a physiological saline absorption of 50 [g/g] and an absorption velocity of 1.8 ml/0.3 g polymer.min].

3 Absorbent retentive sheet (C)

70 parts of rayon for wet process (trade name: Corona (SB) Rayon mfd. by Daiwabo Rayon) having a thickness of 3 denier, a length of 7 mm and a roundness of the section of the fiber of 0.68, 30 parts of pulp fibers and 10 parts of PVA (Gosenol P-250) as a binder were dispersed in water. A paper was prepared from them and dried to obtain and an absorbent sheet having a basis weight of 33 g/m$^2$ and a capillary osmotic pressure of 3,000 dyn/cm$^2$ Hot melt Topko P 618 B (mfd. by Toyo-Petrolite Co., Ltd.) was spirally sprinkled at a rate of 10 g/cm$^2$ over this absorbent sheet and then the highly water-absorbent polymer (B) was sprinkled over it at a rate of 40 g/m$^2$. The absorbent sheet having a basis weight of 33 g/m$^2$ and a capillary osmotic pressure of 3,000 dyn/m$^2$ was placed thereon to form an absorbent retentive sheet (C).

(4) Preparation of surface sheet

1 Surface sheet (A)

A low-density polyethylene (thickness: 25 $\mu$m) (mfd. by Mitsui Petrochemical Industries, Ltd.) was applied to a nonwoven fabric prepared from polyethylene-/polypropylene complex fibers (mfd. by Chisso Corp.) prepared by dry hot gluing method and having 0.34% by weight of a mixed surfactant of an alkyl phosphate-/sorbitan fatty acid ester adhering thereto to form a laminate, thereby obtaining a surface sheet (A) having a density of concavity 1 A formation of 52/cm$^2$ as shown in FIG. 4. The size of the opening 1 C in the side wall 1 B in the concavity 1 A was 0.1 to 2 mm$^2$.

2 Surface sheet (B)

A surface sheet (nonwoven fabric) of a commercially available sanitary napkin (trade name: Rollier mfd. by Kao Corporation) was used as the surface sheet (B).

3 Surface sheet (C)

A hydrophobic sheet of low-density polyethylene (mfd. by Mitsui Petrochemical Industries, Ltd.) having numerous openings having an area of 0.18 mm$^2$ (on average) dispersed over it was used as the surface sheet (C).

EXAMPLE 1

Three diffusing absorbent sheets 21 were used. The diffusing absorbent sheet (B) was used as the top layer to be brought into contact with the skin and two diffusing absorbent sheets (A) were placed below it. The absorbent retentive sheet (A) was placed below them to form a laminate, which was cut to form the absorbent element 2 having a width of 75 mm and a length of 195 mm. A sanitary napkin 1 of the present invention as shown in FIG. 1 was prepared from the absorbent element 2, antileakage sheet 3 laminated with polyethylene, surface sheet (A) 1 and tape 4 for prevention of slipping off.

EXAMPLE 2

A sanitary napkin 2 of the present invention shown in FIG. 1 was prepared in the same manner as that of Example 1 except that the diffusing absorbent sheet (C) was used as the top layer of the three diffusing absorbent sheets 21 and two diffusing absorbent sheets (A) were placed below it.

EXAMPLE 3

An absorbent element 2 was prepared by using the diffusing absorbent sheet (D) as the top layer of the two diffusing absorbent sheets 21 and placing the diffusing absorbent sheet (E) below it, then laminating these two diffusing absorbent sheets 21 with absorbent retentive sheet A 22 placed below it and cutting the laminate to form an absorbent element 2 having a width of 75 mm and a length of 195 mm. A sanitary napkin 3 of the present invention as shown in FIG. 2 was prepared from the absorbent element 2, antileakage sheet 3 laminated with polyethylene, surface sheet (A) 1 and tape 4 for prevention of slipping off.

EXAMPLE 4

A sanitary napkin 4 of the present invention shown in FIG. 1 was prepared in the same manner as that of Example 1 except that all the three diffusing absorbent sheets 21 used were the diffusing absorbent sheets (A).

EXAMPLE 5

A sanitary napkin 5 of the present invention shown in FIG. 1 was prepared in the same manner as that of Example 1 except that all the three diffusing absorbent sheets 21 used were the diffusing absorbent sheets (C).

EXAMPLE 6

A sanitary napkin 6 of the present invention shown in FIG. 1 was prepared in the same manner as that of Example 1 except that the surface sheet (B) was used as the surface sheet.

EXAMPLE 7

A sanitary napkin 7 of the present invention shown in FIG. 1 was prepared in the same manner as that of Example 1 except that the surface sheet (C) was used as the surface sheet.

COMPARATIVE EXAMPLE 1

A comparative sanitary napkin 1 shown in FIG. 1 was prepared in the same manner as that of Example 1 except that all the three diffusing absorbent sheets 21 used were the diffusing absorbent sheets F.

COMPARATIVE EXAMPLE 2

A comparative sanitary napkin 2 shown in FIG. 1 was prepared in the same manner as that of Example 1 except that all the three diffusing absorbent sheets 21 used were the diffusing absorbent sheets (G).

COMPARATIVE EXAMPLE 3

A comparative sanitary napkin 3 shown in FIG. 1 was prepared in the same manner as that of Example 1 except that all the three diffusing absorbent sheets 21 used were the diffusing absorbent sheets (H).

COMPARATIVE EXAMPLE 4

Figure 8:
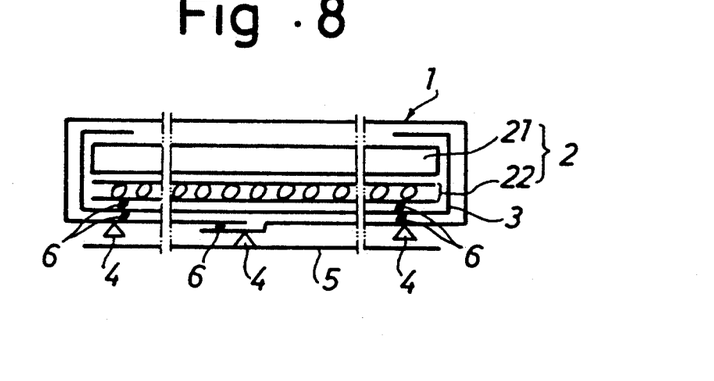
FIG. 8 is a cross section corresponding to that of FIG. 1 which shows a comparative example for the sanitary napkin shown in FIG. 1.

The absorbent sheet (I) was used as the diffusing absorbent sheet 21, which was laminated with the absorbent retentive sheet (A) placed below it as shown in FIG. 8. It was cut to form the absorbent element 2 having a width of 75 mm and a length of 195 mm. A comparative sanitary napkin 4 as shown in FIG. 3 was prepared from the absorbent element 2, antileakage sheet 3 comprising a paper laminated with polyethylene, surface sheet (A) 1 and tape 4 for prevention of slipping off.

COMPARATIVE EXAMPLE 5

A comparative sanitary napkin 5 shown in FIG. 1 was prepared in the same manner as that of Example 5 except that the absorbent retentive sheet B was used as the absorbent retentive sheet 22.

COMPARATIVE EXAMPLE 6

A comparative sanitary napkin 5 shown in FIG. 1 was prepared in the same manner as that of Example 5 except that the absorbent retentive sheet (C) was used as the absorbent retentive sheet 22.

COMPARATIVE EXAMPLE 7

A comparative sanitary napkin 7 shown in FIG. 1 was prepared in the same manner as that of Example 6 except that all the three diffusing absorbent sheets 21 used were the diffusing absorbent sheets (F).

COMPARATIVE EXAMPLE 8

A comparative sanitary napkin 8 shown in FIG. 1 was prepared in the same manner as that of Example 7 except that all the three diffusing absorbent sheets 21 used were the diffusing absorbent sheets (F). II. The absorbent retentive effects of the sanitary napkins 1 through 7 of the present invention obtained in Examples 1 through 7, respectively, and comparative sanitary napkins 1 through 8 obtained in Comparative Examples 1 through 8, respectively, were evaluated by subjecting them to the tests of the dynamic quantity (g) of reflow and leakage tests by the method described below to obtain the results given in Table 2.

(1) DYNAMIC QUANTITY OF REFLOW

Figure 14:
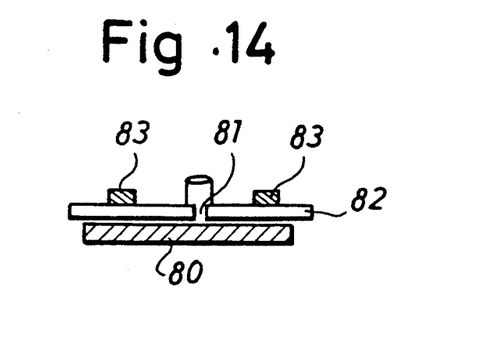
FIG. 14 is a cross section of an apparatus used for the determination of the dynamic quantity of reflow.
Figure 15:
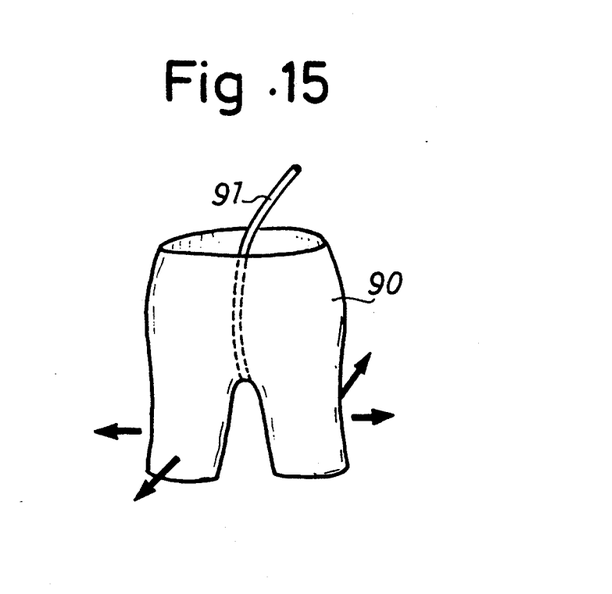
FIG. 15 is a perspective view of a movable model of the hip of a woman.
Figure 16:
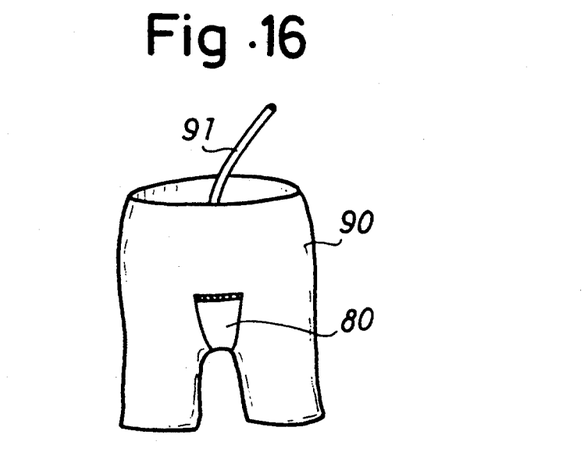
FIG. 16 is a perspective view of the movable model of the hip of a woman wearing a sanitary napkin to be tested.

A sanitary napkin 80 obtained in the Examples or Comparative Examples for testing was horizontally placed and an acrylic plate 82 having an inlet 81 having a diameter of 10 mm was placed thereon as shown in FIG. 14. Weights 83 were placed thereon so that a load of 5 g/cm$^2$ would be applied to the sanitary napkin for testing (the total weight of the acrylic plate 82 and the weights 83 being was 732 g). 10 g of defibrinated equine blood (a product of Nippon Biotest Laboratories) was poured through the inlet 81. After the completion of the pouring, the napkin was left to stand for 20 min. Ten sheets of absorbent paper having a width of 75 cm, a length of 195 mm and a basis weight of 30 g/cm$^2$ were placed on the sanitary napkin 80 (on the side to be brought into contact with the user's skin). The sanitary napkin 80 having the absorbent paper sheets placed thereon was applied to a movable female hip model 90 shown in FIG. 15 as shown in FIG. 16. Shorts were put on it and the model was walked at a walking velocity of 100 steps / min (50 m/min) for 1 min.

Then the sanitary napkin 80 and ten absorbent paper sheets were taken out to weigh the defibrinated equine blood absorbed in the absorbent paper and the obtained weight was defined as the quantity (g) of reflow. Ten sanitary napkins 80 were tested and the average of the quantities of reflow thereof was defined as the dynamic quantity of reflow.

(2) LEAKAGE TESTS

Each of the sanitary napkin 80 obtained in the above-described Examples and Comparative Examples for testing was applied to the movable female hip model 90 as shown in FIG. 15. Short were put on it and the model was walked at a walking velocity of 100 steps/min (50 m/min) for 10 min. Then 3 g of defibrinated equine blood was injected through a tube 91 while walking and thereafter the model was walked at the same walking velocity for 10 min. The injection of 3 g of the defibrinated equine blood followed by walking for 10 min was repeated twice and the number of the sheets wetted by leakage in the 10 samples was counted each time. The results are given in Table 2.

according to the synergism which cannot be obtained when the sheets are used separately from one another.

It will be understood that the absorbent articles 1 through 7 of the present invention comprising the combination of the specified diffusing absorbent sheets and specified absorbent retentive sheet are capable of rapidly absorbing a liquid to effectively exhibit the characteristic properties of the highly absorbent polymer and that they can be made quite thin and make the users comfortable.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

TABLE 1

Composition and properties of diffusing absorbent sheet

| Diffusing absorbent sheet | Composition | $\cos\theta$ | Absorption height after 1 min (mm/min) | Liquid permeation time (s) | Spreading ratio (longitudinal/ transverse) in spread liquid area | Residual strain after compression in wet state |
|---|---|---|---|---|---|---|
| A | SA rayon/pulp blended paper (SA rayon/pulp = 75/25) | 0.85 | 70 | 41 | 1.6 | 0.18 |
| B | SA rayon/pulp blended paper (SA rayon/pulp = 50/50) | 0.70 | 56 | 110 | 1.3 | 0.25 |
| C | rayon/pulp blended paper (rayon/pulp = 70/30) | 0.78 | 53 | 63 | 1.3 | 0.28 |
| D | Nonwoven rayon fabric | 0.97 | 49 | 53 | 1.0 | 0.17 |
| E | Nonwoven rayon fabric | 0.98 | 62 | 58 | 1.0 | 0.15 |
| F | Absorbent paper (pulp 100%) | 0.44 | 33 | 272 | 0.7 | 0.42 |
| G | SA rayon/pulp blended paper (SA rayon/pulp = 10/90) | 0.47 | 37 | 220 | 1.1 | 0.38 |
| H | Rayon/pulp blended paper (rayon/pulp = 50/50) | 0.68 | 25 | 125 | 1.2 | 0.30 |
| I | Pulp sheet | — | — | — | 1.0 | 0.45 |

TABLE 2

| | Diffusing absorbent sheet | Absorbent retentive sheet | Surface sheet | Dynamic quantity of reflow (g) | Number of times of leakage 3 g | 6 g | 9 g |
|---|---|---|---|---|---|---|---|
| Present invention | | | | | | | |
| 1 | B + A | A | A | 0.1 | 0 | 0 | 0 |
| 2 | C + A | A | A | 0.2 | 0 | 0 | 1 |
| 3 | D + E | A | A | 0.3 | 0 | 0 | 3 |
| 4 | A | A | A | 0.3 | 0 | 0 | 3 |
| 5 | C | A | A | 0.5 | 0 | 0 | 4 |
| 6 | B + A | A | B | 0.5 | 0 | 3 | 5 |
| 7 | B + A | A | C | 0.5 | 0 | 2 | 4 |
| Comparative | | | | | | | |
| 1 | F | A | A | 0.8 | 1 | 5 | 9 |
| 2 | G | A | A | 0.7 | 0 | 4 | 8 |
| 3 | H | A | A | 1.0 | 2 | 6 | 10 |
| 4 | I | A | A | 1.0 | 1 | 6 | 10 |
| 5 | C | B | A | 0.7 | 0 | 5 | 7 |
| 6 | C | C | A | 0.7 | 0 | 6 | 8 |
| 7 | F | A | B | 1.2 | 3 | 8 | 10 |
| 8 | F | A | C | 1.0 | 2 | 7 | 10 |

(3) It is apparent from the results given in Table 2 that the absorbent articles 1 through 7 of the present invention comprising the combination of the specified diffusing absorbent sheets and absorbent retentive sheet exhibited a remarkably increased absorbent capacity, only a small quantity of reflow and only a slight leakage

What is claimed is:

1. An absorbent article comprising a liquid-permeable outer material, a liquid-impermeable antileakage material and a liquid-retentive absorbent element interposed therebetween, and formed in a substantially vertically elongated shape having a longitudinal dimension, wherein the absorbent element comprises a diffusing absorbent sheet having a front surface and a rear surface, and an absorbent retentive sheet positioned between said rear surface of said diffusing absorbent sheet and said liquid-impermeable antileakage material, and wherein:

(a) the diffusing absorbent sheet is at least one sheet having a hydrophilicity, said hydrophilicity defined as a cosine of a contact angle between a liquid and a solid surface angle, of 0.5 and 1 and a Klemm absorption velocity in a direction along said longitudinal dimension of at least 40 mm/minute; and (b) the absorbent retentive sheet is at least one sheet comprising an aggregate of fibers having a capillary osmotic pressure of 4,000 to 15,000 dyne/cm$^2$ and containing 10 to 100% by weight, based on the fiber aggregate, of a highly water-absorbent polymer having a physiological saline absorption of 40 to 70 grams physiological saline per gram polymer and a physiological saline absorption velocity of at least 2 ml/0.3 grams polymer.minute.

2. The absorbent article according to claim 1, wherein the diffusing absorbent sheet is a wet-process nonwoven fabric made of hydrophilic fibers.

3. The absorbent article according to claim 1 or 2, wherein said diffusing absorbent sheet has a Klemm absorption velocity gradient, wherein the velocity is increased from said front surface toward said rear surface of said diffusing absorbent sheet.

4. The absorbent article according to claim 1, wherein the diffusing absorbent sheet has a liquid permeation time of not longer than 200 seconds when an 85% aqueous glycerol solution is dropped thereon.

5. The absorbent article according to claim 1, wherein said diffusing absorbent sheet has a liquid spread area, and wherein a longitudinal/transverse ratio of said liquid spread area obtained one minute after dropping physiological saline is at least 1.2.

6. The absorbent article according to claim 1, wherein said diffusing absorbent sheet has a residual strain after compression of 0.3 or below when said diffusing absorbent sheet contains a liquid absorbed therein.

7. The absorbent article according to claim 1, wherein the diffusing absorbent sheet comprises a blended paper of rayon fibers and pulp fibers, said rayon fibers having a denier of less than 3, and wherein an amount of said rayon fiber in said blended paper is 30 to 90% of fibers in said blended paper.

8. The absorbent article according to claim 1, wherein the rayon fiber has a roundness of 0.5 or less.

9. The absorbent article according to claim 1, wherein said liquid-permeable outer material comprises a film layer and a hydrophilic fiber aggregate layer between said film layer and said liquid-retentive absorbent element, said two layers being integral with each other, and having numerous concavities having center tacks said concavity having walls which incline toward said centers, and has openings in said film layer on at least said inclined walls of said concavities.

10. The absorbent article of claim 1, wherein the diffusing absorbent sheet is a material selected from the group consisting of polyurethane, polystyrene, polyethylene, polyester, polyvinyl alcohol, butadiene-styrene rubber, nitrile-butadiene rubber fiber aggregates produced by bonding synthetic fibers, and fiber aggregates produced by bonding hydrophilic fibers.

11. The absorbent article of claim 1, wherein when the diffusing absorbent sheet is made of a hydrophobic material, said material contains a surfactant to impart hydrophilic properties thereto.

12. The absorbent article of claim 11, wherein the surfactant is selected from the group consisting of sulfosuccinic esters, alkyl ether sulfates, polyoxyethylene alkyl ethers, polyoxyethylene alkylphenol ethers and glycerol fatty acid esters.

13. The absorbent article of claim 1, wherein the diffusing absorbent sheet is a laminate of two or more layers.

14. The absorbent article of claim 1, wherein the diffusing absorbent sheet is a single layer.

15. The absorbent article of claim 1, wherein said absorbent retentive sheet is a laminate of two fiber sheets, each having a capillary osmotic pressure of 4,000 to 15,000 dyne/cm$^2$ separated by a highly absorbent polymer sheet having a physiological saline absorption of 40 to 70 grams physiological saliny per gram polymer and a physiological saline absorption velocity of at least 2 ml/0.3 gram polymer.minute interposed between said two fiber sheets in an amount of 10 to 100% by weight based on a total weight of the aggregate of fibers comprising said two fiber sheets.

16. The absorbent article of claim 1, wherein said absorbent article is a sanitary napkin.

17. The absorbent article of claim 1, wherein said absorbent article is a paper diaper.

18. The absorbent article of claim 1, wherein said absorbent article is an absorbent pad.

* * * * *